United States Patent
Kanakaris et al.

(10) Patent No.: US 6,210,343 B1
(45) Date of Patent: Apr. 3, 2001

(54) USE OF MISOPROSTOL OR/AND MISOPROSTOL ACID FOR DIAGNOSIS OF VASCULAR DAMAGE IN A SUBJECT WITH ERECTILE DYSFUNCTION

(76) Inventors: Panagiotis Kanakaris, 33 Koletti Street, GR-106, 77 Athens; Petros Karouzakis, 9 Bakou Street, GR-115, 24 Athens, both of (GR)

(*) Notice: Subject to any disclaimer, the term of this patent is extended or adjusted under 35 U.S.C. 154(b) by 0 days.

(21) Appl. No.: 09/423,130
(22) PCT Filed: Apr. 22, 1998
(86) PCT No.: PCT/GR98/00012
§ 371 Date: Dec. 29, 1999
§ 102(e) Date: Dec. 29, 1999
(87) PCT Pub. No.: WO98/50039
PCT Pub. Date: Nov. 12, 1998

(30) Foreign Application Priority Data

May 6, 1997 (GR) ................................. 970100172

(51) Int. Cl.[7] ................ A61B 5/00; A61B 7/00; A61B 5/103; A61K 31/19; A61K 31/557

(52) U.S. Cl. .................. 600/504; 600/301; 600/586; 600/587; 514/929; 514/573

(58) Field of Search ................... 514/573, 530, 514/58, 922, 929, 946, 947

(56) References Cited

PUBLICATIONS

Vidal Moreno et al., Assessment of tobacco impact on penile vascularization with echo–Doppler and intracavernous injection, Servicio de Urologia, Hospital Universitario La Fe Valencia, see abstract, Dec. 1996.*

* cited by examiner

Primary Examiner—Frederick Krass
Assistant Examiner—Donna Jagoe
(74) Attorney, Agent, or Firm—Bromberg & Sunstein LLP

(57) ABSTRACT

A method is provided for diagnosing vascular damage in a subject with erectile dysfunction that includes applying an effective dose of a therapeutic formulation having an excipient and at least one of misoprostol and misoprostolic acid topically to the glans penis of the subject and determining the vascular damage by the Doppler method or cavernosometry

3 Claims, No Drawings

USE OF MISOPROSTOL OR/AND MISOPROSTOL ACID FOR DIAGNOSIS OF VASCULAR DAMAGE IN A SUBJECT WITH ERECTILE DYSFUNCTION

The invention relates to the use of an already known pharmaceutical substance, misoprostol as well as its first metabolite, misoprostol acid, for the preparation of a drug for external use which is destined to cure erectile dysfunction. Nowadays the pharmaceutical treatment of erectile dysfunction—except of the cases of hormonal insufficiency, which are generally rare and in which a suitable substitution therapy is followed—includes mainly the use of intracavernosous injections consisting in the direct injection of vasodilatory drugs (papaverine, phentolamine and alprostadil) into the corpora cavernosa of the penis (Campell's Urology, ed. W. B. Saunders Company, $6^{th}$ edition, volume III, p.3055–3057). Although this method is the most efficient and perhaps the only scientifically acceptable, it has the serious disadvantage of the form (injection) as well as the manner of administration intracavernosal. Yohimbin, an $a_2$-adrenergic inhibitor, is administrated per os, however the efficiency of this old method is doubtful (Campell's Urology, ed. W. B. Saunders Company, $6^{th}$ edition, volume III, p.3053).

In former times the topical application of a nitroglycerin paste had been proposed (Claes et al 1989), but the method was not therapeutically applied because of doubtful efficacy and serious side-effects (Campell's Urology, ed. W. B. Saunders Company,$6^{th}$ edition, volume III, p.3053). The topical application of prostaglandin $E_1$ (or alprostadil) in the form of an endourethral gel or stick as a means of limited efficacy in the therapy of male impotence of a vascular cause (International Journal of Impotence Research, Stocton ed., vol. 7, September 1995, supplement I, p.05–06) was recently proposed we must note that the discovery of vasodilatory drugs with sufficient transcutaneous absorption or the use of methods (e.g.ionophoresis) which can reinforce the penetration of such drugs through the skin of the mucosal membranes, inside the corpora cavernosa of the penis has for long attracted the interest of many research workers (Campell's Urology, ed. W. B. Saunders Company, $_6^{th}$ ed. vol. III, p.3057)

Up to day a common denominator of the methods destined for external application is mainly the low efficacy combined with increased therapy cost and the apparition of more or less serious side-effects.

But the most serious technical difficulty that can be especially confronted by the methods for external use, is that drugs must penetrate through the various barriers of the skin and the mucosals and reach—in a satisfactory gathering—into the corpora cavernosa in order to act. The present method aims at the removal of the drawbacks of the above methods using misoprostol in the symptom therapy of male impotency. Misoprostol is the general name of a synthetic prostaglandin belonging to the $E_1$ series ($PGE_1$ analogs). Synthesis: P. W. Collins, R Pappo, Belgian patent 827.127, U.S. Pat. No. 3,965,143 (The Merck Index, ed. Merck & Co. Inc, $11^{th}$ edition, 1989, p. 6128).

Its chemical name is (11a, 13E)-(±)-11, 16-Dihydroxy-16-methyl-9-oxoprost-13-en-1-oic acid methyl ester or (±)-(methyl)-(1R, 2R, 3R)-3-hydroxy-2-[(E)-(4RS)-4-hydroxy-4-methyl-1-octenyl]-5-oxocyclopentaneheptanoate or (±)-15-deoxy-(16RS)-16-hydroxy-16-methyl-$PGE_1$ methyl ester.

It is consisted of 4 stereoisomers in about equal proportions [(+)&(−) enantiomers of 16R- and 16S-forms]. (The Merck Index, $11^{th}$ edition, 1989, p. 6128). The empirical formula is $C_{22}H_{38}O_5$. Its structural formula appears in FIG. I.

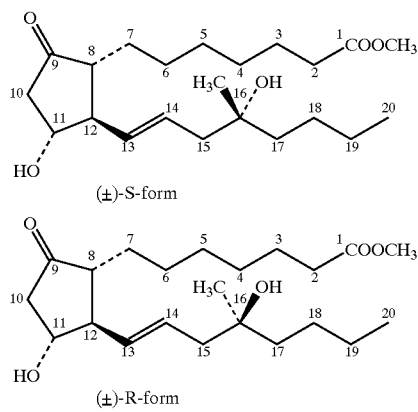

FIG. I.

(±)-S-form (±)-R-form

Compared with other prostaglandins of group $E_1$ and especially alprostadil, misoprostol bears a methyl group ($-CH_3$) on the carbon atom of position 16.

According to a method which relates the biological action of various medicament molecules to its chemical structure (Method of Minimum Stereochemical Difference, "Planning of drugs", P. Kourounakis-E. Rekka, ed. Graphical Arts, Thessaloniki, 1992, p. 152) it appears that due to this group we have a big penetration of misoprostol in the underlying tissues and a local vasodilation which cures erection dysfunctions. Misoprostol is used today orally as antiulcer drug (Physicians Desc Reference, PDR, ed. Medical Economics Data, Production Company at Montrale $48^{th}$ edition, 1994, P. 2197–2199).

In particular it is administered for the prevention of gastric ulcer to patients who take non-steroid antiinflammatory drugs. It is available in the countries of Europe and U.S.A. by Searle Company under the commercial name Cytoteco®. In none country is the drug mentioned as suitable for male impotence nor are there any relevant reports on the international bibliography. On a contrary amongst the undesirable effects in oral therapy with misoprostol is male impotence (Physicians Desc Reference, ed. Medical Economics Data, Production Company at Montrale, $48^{th}$ edition, 1994, p. 2197–2199).

Misorostol instead of the fact that creates slighter vasodilatory action, compared to alprostadil when provided intracavernosaly, it does cause larger vasodilation when applicated externaly. This is happening because the action mechanism on the erectile function among misoprostol and other vasodilatories (e.g. alprostadil) seriously differs. Misoprostol applicated topically penetrates through the corpora cavernosa and creates slight action-compared to other vasodilatories-onthesmooth muscle fibres of the vessels. But, its main action is revealed atthe gland vessels and in a smaller degree at the prepuce.

Because of the strong topical vasodilation, into the intense bleed of these vessels is caused. Consequently as natural, a negative pressure into the corpora cavernosa is created, and is getting balanced by the abundant blood entrance into these, finally resulting at the provocation of erection. In other words, the gland vessels act as "blood pumps" and by that mechanism the erectile function is getting operated at once.

On the other hand due to the fact that the degree of response to a small dose of misoprostol (durability and hardness of erection) depends on the physiological condition and function of the penile vessels, misoprostol can be used as accessory diagnostic means (instead of papaverine or alprostadil) in the "Doppler" method or the cavernosometry, for the determination of the extent and kind of vascular damage (about the use of vasodilatory drugs as accessory diagnostic means in the "Doppler" method or cavernosometry, see Erektile Impotenz, ed. Enke, p.68–77 & p. 88–110).

Equally strong topical vasodilatory action after external application is exerted by the hydrolysis product of misoprostol, (misoprostol acid) which anyway constitutes the first misoprostol metabolite after its introduction in the organism (see FIG.II).

FIG. II.

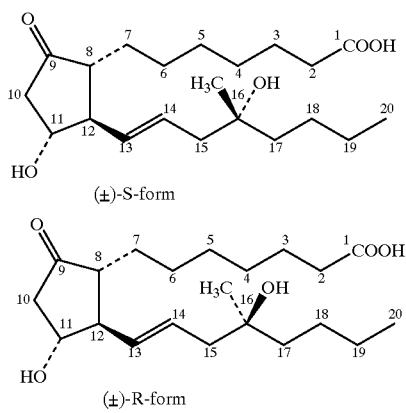

(±)-S-form (±)-R-form

Finally because of the topical vasodilatory action of misoprostol and the relative free acid, both pharmaceutical molecules facilitate the absorption of other drugs through the skin and the mucosals. In other words, they act as "penetration enhancers". Especially regarding to vasodilatory substances (e.g. alprostadil) on the one hand it facilitates the passing through the skin and the mucosals, resulting to high gatherings of these drugs into the tissues and especially into the corpora cavernosa and on the other hand it expresses a synergic action with them. Misoprostol can be dissolved in water and its compatibility with excipients provides the opportunity of production of a variety of simple pharmacotechnical forms for external use, which are at the same time very well tolerated by the skin and the mucousa. From the above mentioned description it appears that the most serious advantage of the method is the manner of administration of the drug (external in combination with the lack of undesirable action in the suggested doses or/and the proposed pharmacotechnical forms) the relatively low cost and especially the most satisfactory result together with corresponding methods.

But mostly, with the application of the described method a serious technical difficulty is getting overcome. Actually the difficulty for a drug to pass through various barriers of the skin and the mucosal and reach in a satisfactory gathering at the corpora cavernosa in order to actis overcome". Amongst the probable methods of application, most advantageous is a synthesis in the gel form of relatively low viscosity which contains 0, 9 % w/v misoprostol in the methylform of methylester and/or free acid, a complexforming means, as 1, 6% w/v a-cyclodextrine and substances suitable for the formation of a gel e.g. hydroxypropyl methylcellulose "3000" 2% w/v, propylene glycol 10% v/v and Water to 100 ml. The gel contains 9 mg of active substance per ml.

Method of application: 0, 1–0, 25 ml (or more, depending on responce) are pasted or spread on the glans of penis. 9 examples related to the pharmacotechnical forms and the ways of application of misorostol:

1) 0,05–0, 20 ml gel, relatively low viscosity containing 0, 9% w/v misoprostol to apply on the glans of the penis or on the prepuce.

| Synthesis: | |
| --- | --- |
| 1-1.Misoprostol | 0,9 g |
| Hydroxypropyl Methylcellulose "3000" | 2 g |
| Water purified to | 100 ml |
| 1-2.Misoprostol | 0,9 g |
| Sodium Carboxymethylcellulose | 2 g |
| Propylene Glycol | 25 ml |
| Water purified to | 100 ml |

2) 0.05–0.20 ml gel of relatively high viscosity, containing 0.50% w/v in misoprostol for endourethral application at a depth 2–5 cm from the outside urethra opening.

| Synthesis: | |
| --- | --- |
| 2-1.Misoprostol | 0,50 g |
| Hydroxypropyl Methylcellulose "3000" | 4 g |
| Water purified to | 100 ml |
| 2-2.Misoprostol | 0,50 g |
| Sodium Carboxymethylcellulose | 4 g |
| Propylene Glycol | 25 ml |
| Water purified to | 100 ml |

3) 0.05–0.20 ml of aqueous solution of misoprostol containing 0.9% w/v for spreading on the glans of the penis or of the prepuce. The solution can also contain propylene glycol or glycerol in the corresponding proportions (e.g. 10%) to increase the viscosity of the solution.

4) 0.05–0.20 ml of ointment or emulsion of containing 0.9% w/w misoprostol for apply on the glans of the penis or on the prepuce, where misoprostol is found spread in the continuous (aqueous) phase.

| Synthesis: | |
| --- | --- |
| 4-1.Misoprostol | 0,9 g |
| Vanishing Cream to | 100 g |

(Although for the requirements of this example as Vanishing Cream we used bepanthéne® Cream of Roche, we have various creams o/w which are available in commerce or are described in National Pharmacopoeies and can be used for the same purpose).

5) Endourethral sticks of suitable dimensions, weight about 500 mg, containing 0, 04–0, 20% w/w misoprostol to apply on the urethral mucosa.

| Synthesis: | |
| --- | --- |
| 5-1.Misoprostol | 0,04–0,20 g |
| Glycerol | 70 g |
| Gelatine | 20 g |
| Water purified to | 100 g |

6) 0, 05–0,25 ml gel (or more depending of response) according to the examples (1-1) and (2-1) which contains moreover 1, 6% w/v a-cyclodextrine.

7)0, 05–0,25 ml gel (or more depending of response) according to the example (6) which contains moreover 10 ml ethyl alcohol 96° and 0, 5 mg/ml alprostadil.

Notes: 1) The incorporation of misoprostol in bases already mentioned took place in normal temperature (20–25° C.) and at a temperature not exceeding 40° C.
2) No significant changes in misoprostol activity was observed as a function of pH, we observent however an important reduction or/and neutralization of misoprostol action in the presence of Polysorbate "80".
3) The time of appearance of the result varies from 20–40 minutes. The timing of the appearance and the intensity of the result seems to be able been positively influenced by certain moisturising agents (e.g. Propylene Glycol, Glycerol) as well as by certain substances which reinforce by various mechanisms the transcutaneous absorption (e.g. Urea, Acid Citric).

High once only doses of misoprostol (>1800 mcg on the glans of the penis and >1000 mcg in the urethra) cause certain systematic undesirable effects as shudder, feeling of hard ship, excitement and diarrhea. The presence of a-cycodextrine reduces the undesirable effects and allows the application once only of higher doses (>2000 mcg) without notable effect on the timing of its action but with positive effect on the intensity result and with prolonging of its duration.
5) The doses which are mentioned in the examples are only indicative since the intensity of the result depends, apart from the cause and the grade of the erectile dysfunction on other factors as e.g. the degree of moisturising of the underlying tissue, the physiological situation of the skin or the mucosa etc. As had already been mentioned, misoprostol is an extremely hydrophile molecule compared with other prostaglandins of $E_1$ series (e.g. with alprostadil which can be dissolved in alcohol but her solubility in water is only 8000 mcg/100 ml at 35° C.). This consists an important advantage:
   a) Because no use of organic factors is required (e.g. ethyl alcohol) which usually irritate tissues and are thus unsuitable for application on the skin and especially the mucus.
   b) Because it allows the incorporation of active substances on a very small amount of excipient, suitable for application on surfaces of limited extent, as e.g. the urethra or the glans of the penis.
6) Because of the described irritation of the uterine fibers (Physicians Desc Reference, ed. Medical Economics Data, Production Company at Montrale, $48^{th}$ edition, 1994, p. 2197–2199) misoprostol must not contact the female genital apparatus.

What is claimed is:

1. A method for diagnosis of vascular damage in a subject with erectile dysfunction, comprising:
   (a) obtaining an effective dose of a therapeutic formulation having an excipient and at least one of misoprostol and misoprostol acid;
   (b) applying the effective dose topically to the glans penis of the subject; and
   (c) determining vascular damage by the Doppler method or cavernosometry.

2. A method for diagnosis of vascular damage according to claim 1, where vascular damage is determined by the Doppler method.

3. A method for diagnosis of vascular damage according to claim 1, where vascular damage is determined by cavernosometry.

* * * * *